US007740582B2

(12) United States Patent
Miyazawa

(10) Patent No.: US 7,740,582 B2
(45) Date of Patent: Jun. 22, 2010

(54) ULTRASONIC OPERATING APPARATUS

(75) Inventor: Taro Miyazawa, Hino (JP)

(73) Assignee: Olympus Optical Co., Ltd., Tokyo (JP)

( * ) Notice: Subject to any disclaimer, the term of this patent is extended or adjusted under 35 U.S.C. 154(b) by 476 days.

(21) Appl. No.: 10/442,244

(22) Filed: May 20, 2003

(65) Prior Publication Data

US 2004/0039375 A1 Feb. 26, 2004

(30) Foreign Application Priority Data

May 22, 2002 (JP) .............................. 2002-148167

(51) Int. Cl.
*A61B 8/00* (2006.01)
(52) U.S. Cl. ........................ 600/437; 600/439; 600/443; 600/447; 601/2; 601/3; 601/4
(58) Field of Classification Search .................. 604/22; 606/1; 600/439, 437, 443, 447; 601/2–4; 310/314–317
See application file for complete search history.

(56) References Cited

U.S. PATENT DOCUMENTS

| 4,827,911 | A | * | 5/1989 | Broadwin et al. ............... 601/4 |
| 5,255,669 | A | * | 10/1993 | Kubota et al. ................... 601/3 |
| 5,285,792 | A | | 2/1994 | Sjoquist et al. |
| 5,487,386 | A | * | 1/1996 | Wakabayashi et al. ......... 600/437 |
| 5,867,091 | A | * | 2/1999 | Chard ........................ 340/426.26 |
| 5,899,852 | A | | 5/1999 | Takahashi et al. |
| 6,013,048 | A | * | 1/2000 | Podany et al. ................... 604/22 |
| 6,053,906 | A | * | 4/2000 | Honda et al. .................... 606/1 |
| 6,176,840 | B1 | * | 1/2001 | Nishimura et al. ............. 601/2 |
| 6,216,539 | B1 | * | 4/2001 | Johnson et al. ................. 73/592 |
| 6,438,405 | B1 | * | 8/2002 | Mooney et al. .............. 600/427 |
| 6,524,245 | B1 | * | 2/2003 | Rock et al. ................... 600/437 |
| 6,656,119 | B2 | * | 12/2003 | Sasaki et al. ................. 600/437 |
| 6,986,686 | B2 | * | 1/2006 | Shibata et al. ............... 439/650 |
| 7,045,780 | B2 | * | 5/2006 | Kley .......................... 250/306 |

FOREIGN PATENT DOCUMENTS

| JP | 03294150 A | * | 12/1991 |
| JP | 04005542 A | * | 1/1992 |
| JP | 5-23347 | | 2/1993 |
| JP | 6-38973 | | 2/1994 |
| JP | 3081674 | | 6/2000 |
| JP | 2000-287989 | | 10/2000 |
| JP | 2001-120571 | | 5/2001 |
| JP | 2002-017743 | | 1/2002 |
| WO | WO 98/36336 | | 8/1998 |

* cited by examiner

*Primary Examiner*—Brian Casler
*Assistant Examiner*—Baisakhi Roy
(74) *Attorney, Agent, or Firm*—Scully, Scott, Murphy & Presser, P.C.

(57) ABSTRACT

An ultrasonic operating apparatus of the present invention includes an apparatus main body having a vibration driving circuit for generating a driving signal to apply ultrasonic vibrations to a vibration generating portion of a hand piece and having a control portion for generating the driving signal and for systematically controlling the apparatus. An operating and display panel and a water supply pump are arranged to an outer surface of the apparatus main body, and the driving signal is supplied to the hand piece via a connector. Until a user carries out a correct processing routine, the control portion does not perform the above control operation even though the user may execute another control operation. Further, the control portion controls an operation so that an incorrect processing routine is notified to the user on the operating and display panel.

14 Claims, 4 Drawing Sheets

ULTRASONIC OPERATING APPARATUS

This application claims benefit of Japanese Application No. 2002-148167 filed in Japan on May 22, 2002, the contents of which are incorporated by this reference.

BACKGROUND OF THE INVENTION

1. Field of the Invention

The present invention relates to an ultrasonic operating apparatus, and more particularly, to an ultrasonic operating apparatus which timely notifies a user's mistake and thus enables smooth operation.

2. Related Art Statement

In general, an ultrasonic operating apparatus for transmission of ultrasonic vibrations to the organ in the coelom and for resection is well-known.

Various types of the above-mentioned ultrasonic operating apparatuses are conventionally proposed. For example, Japanese Unexamined Patent Application Publication No. 5-23347 discloses an ultrasonic operating apparatus comprising an ultrasonic output portion, a water supply portion, and an absorbing portion, wherein the apparatus is systematically controlled so that the water supply portion and the absorbing portion are operated synchronously with the ultrasonic output.

Generally, the ultrasonic operating apparatus supplies water to clean the organ and to suppress the heating of a probe.

In the above-mentioned ultrasonic operating apparatus, the calorific value of the probe is proportional to an amplitude generated by ultrasonic vibrations and therefore a necessary amount of supplied water changes depending on the amplitude. Consequently, in Japanese Unexamined Patent Application Publication No. 6-38973 discloses, an ultrasonic operating apparatus as one related-art comprises the basic structure disclosed in Japanese Unexamined Patent Application Publication No. 5-23347, wherein the amount of supplied water is controlled in accordance with a setting value of the ultrasonic vibration.

Further, Japanese Patent Publication No. 3081674 proposed by the present applicant discloses an ultrasonic operating apparatus for preventing to start a vibrating operation upon an incomplete preparing state due to the user's mistake and for the safe usage.

OBJECTS AND SUMMARY OF THE INVENTION

Briefly, an ultrasonic operating apparatus comprises: a hand piece having a vibration generating portion for generating ultrasonic vibrations; an ultrasonic operating tool having a probe for transmitting the ultrasonic vibrations to the organ; a signal generating portion which generates a driving signal for applying the ultrasonic vibrations to the vibration generating portion of the hand piece; a control portion which controls the driving signal and systematically controls the apparatus; a detecting portion which detects an abnormal state of the ultrasonic operating tool; and a notifying portion which notifies the abnormal state of the ultrasonic operating tool, wherein the control portion controls an operation so as to prevent the control operation even if another control operation is executed until a user copes with the abnormal state by a correct processing routine and the notifying portion sends a notification indicating the incorrect processing routine to the user.

These objects and advantages of the present invention will become further apparent from the following detailed explanation.

DETAILED DESCRIPTION OF THE PREFERRED EMBODIMENTS

Hereinbelow, embodiments of the present invention will be described with reference to the drawings.

First Embodiment

Figure 1:
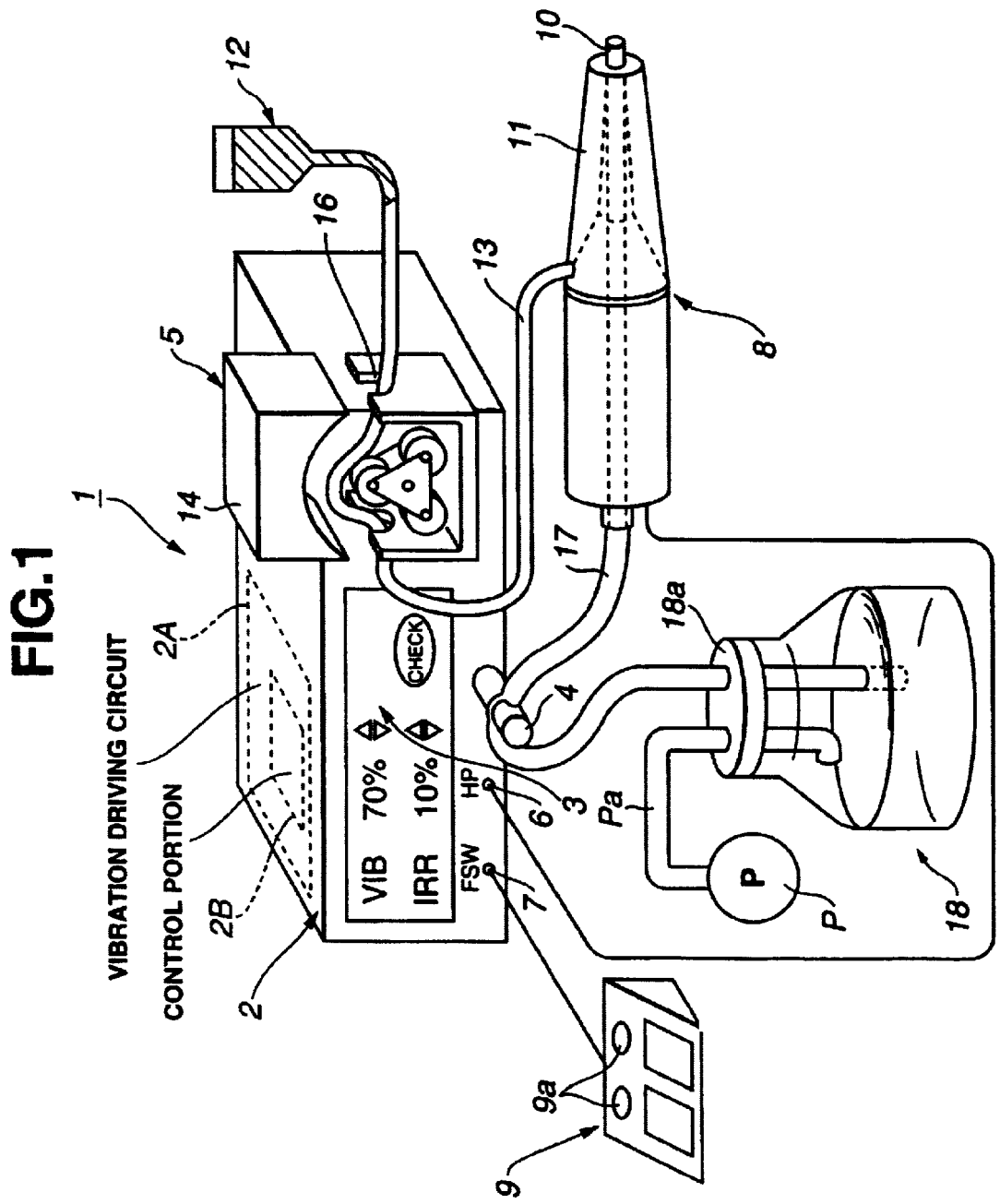
FIG. 1 is a block diagram schematically showing the system structure of an ultrasonic operating apparatus according to a first embodiment of the present invention.
Figure 2:
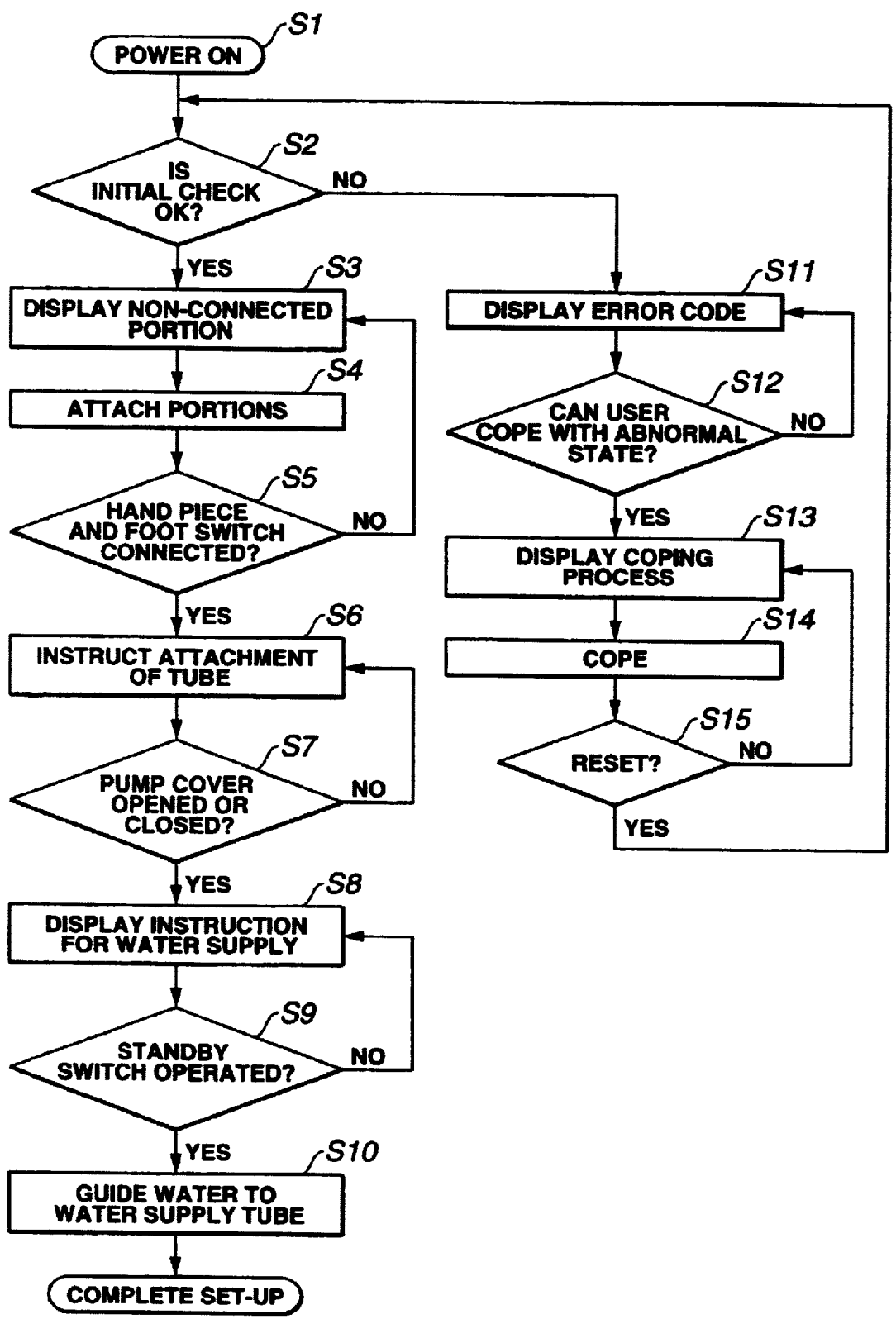
FIG. 2 is a flowchart showing an example of a control operation characterized by a control portion in the ultrasonic operating apparatus.

FIGS. 1 and 2 show an ultrasonic operating apparatus according to the first embodiment of the present invention, FIG. 1 is a block diagram schematically showing the system structure of the ultrasonic operating apparatus 1, and FIG. 2 is a flowchart showing an example of a control operation characterized by a control portion in the ultrasonic operating apparatus 1.

(Structure)

Referring to FIG. 1, the ultrasonic operating apparatus 1 according to the first embodiment comprises an apparatus main body 2 as a main apparatus of the ultrasonic operating apparatus 1, and the apparatus main body 2 comprises a control portion 2B for systematically controlling the ultrasonic operating apparatus 1 and a vibration driving circuit 2A.

Further, the apparatus main body 2 comprises an operating and display panel 3, a pinch valve 4, a water supply pump 5, and connectors 6 and 7 on an outer surface thereof.

The operating and display panel 3 has an integral arrangement of a display member such as an LCD and an operating button, sets various processing, displays the type of a selected operation and an operating state, and performs various operations.

A plug of a hand piece 8 is detachably connected to the connector 6 and a driving signal from the vibration driving circuit 2A is transmitted to the hand piece 8 via the connector 6. A foot switch 9 detachably connected to the connector 7 controls the operation of the driving signal in this case. An arbitrary number of switches 9a are provided to the foot switch 9 in accordance with the necessary output operation. A foot easily operates the switches by using the switch 9a.

An ultrasonic vibrator (not shown) is integrated with a horn for enlarging the amplitude in the hand piece 8. A probe 10 is detachably attached to an edge of the hand piece 8.

Further, a sheath 11 is attached on a front end side of the hand piece 8 to cover the probe 10, and a water supply passage is formed between the probe 10 and the sheath 11. In this case, the probe 10 is exposed to the outside of an edge of the sheath 11.

A flexible water supply tube 13 for connection to the water supply passage of the sheath 11 is connected to a water supply tank 12 containing saline, via a water supply path. The water supply tube 13 is detachably attached to the water supply pump 5 by an opening and closing operation of a pump cover 14 of the water supply pump 5.

As shown in FIG. 1, the water supply pump 5 comprises: a pump cover 14 for holding the water supply tube 13; a link mechanism (not shown) for executing the opening and closing operation of the pump cover 14; opening and closing detecting means (not shown) which detects the opening and closing operation of the pump cover 14 in accordance with the operation of the link mechanism; and a tube guide portion 16 which is arranged on both-end sides of the water supply pump 5 and which protects the water supply tube 13 at an unspecified portion of the pump cover 14 upon opening and closing the pump cover 14.

Here, upon opening and closing the pump cover 14, the opening and closing detecting means detects the opening and closing operation of the pump cover 14 via the link mechanism (not shown), and outputs a detection result to the control portion 2B. In accordance therewith, the control portion 2B recognizes the opening and closing operation of the pump cover 14.

The tube guide 16 is arranged on both-end sides of the water supply pump 5 and, thus, the water supply tube 13 is accommodated in an inner groove of the tube guide 16 and maintains its proper position for supplying the water. Consequently, upon opening and closing the pump cover 14, it is possible to prevent the damage of the water supply tube 13 due to the sandwiching thereof by the unspecified portion of the pump cover 14.

As mentioned above, according to the first embodiment, water supply means for cooling the probe 10 is provided.

On the other hand, a hollow hole for inner connection is provided from an inner portion of the probe 10 to another end of the hand piece 8, thereby forming an absorbing passage. A flexible absorbing tube 17 for connecting to the absorbing passage is attached from a rear end side of the hand piece 8. Another end of the absorbing tube 17 is fixed by a cover portion 18a in a state in which it is inserted in an absorbing bin 18 for removing an absorbing material. One end of an absorbing tube Pa is inserted in the absorbing bin 18 by the cover portion 18a and another end thereof is connected to an absorbing pump P for generating absorbing force.

As mentioned above, according to the first embodiment, absorbing means for absorbing and removing the supplied water is provided.

According to the first embodiment, in the ultrasonic operating apparatus 1 with the above structure, the control portion 2B in the apparatus main body 2 prevents an operating default of the apparatus which is caused by a user's operating mistake and controls various processing to use the apparatus safely.

(Operation)

Figure 3:
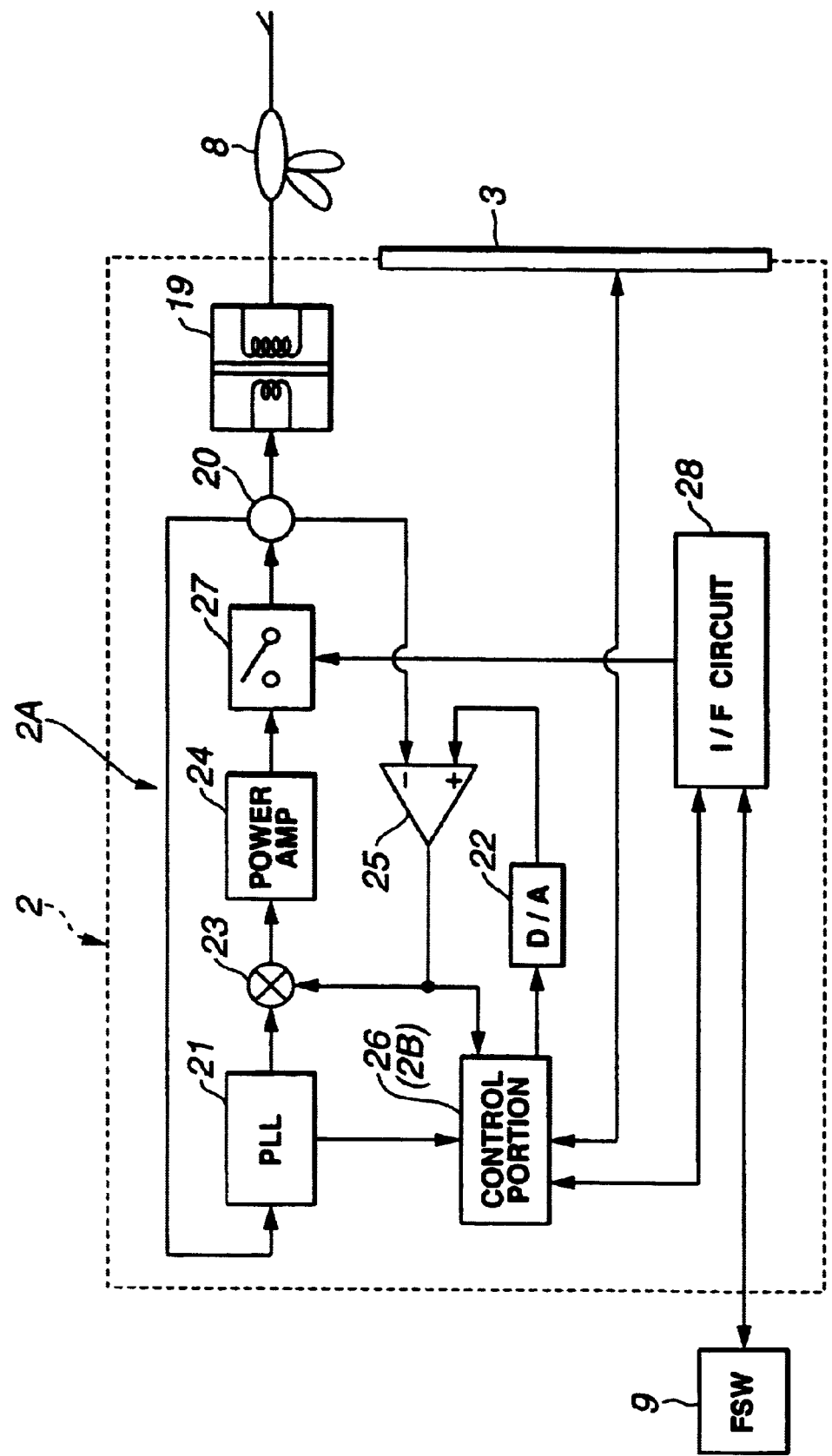
FIG. 3 is a block diagram showing the structure of a vibration driving circuit in an improved ultrasonic operating apparatus according to a second embodiment of the present invention.

Next, a detailed description is given of an example of a control operation characterized by the control portion in the ultrasonic operating apparatus 1 according to the first embodiment with reference to FIG. 3.

Treatment is performed by using the ultrasonic operating apparatus 1 shown in FIG. 1. In this case, a user turns on power of the apparatus main body 2 and then the control portion 2B in the apparatus main body 2 starts a processing routine shown in FIG. 2. In step S1, the control portion 2B recognizes on-power and, then, in step S2, the control portion 2B performs initial check of the apparatus main body 2. Only when the control portion 2B determines in step S2 that no abnormal state is caused, the processing routine advances to step S3 and sequential steps. On the contrary, when the control portion 2B determines in step S2 that any abnormal state is caused, the abnormal state is notified to an operator by processing in steps S11 to S15 by using a process for displaying the abnormal state with a specified character and sound. Until the abnormal state is solved, the processing routine returns to step S2 whereupon the control portion 2B performs the operation so that the initial check is executed again.

When the control portion 2B determines that the abnormal state is found, specifically, in step S11, the control portion 2B displays an error code on the operating and display panel 3. In step S12, the control portion 2B determines whether or not the user can cope with the abnormal state. When it is determined in step S12 that the user can cope with the abnormal state, in step S13, a coping process is displayed on the operating and display panel 3. In step S14, the user performs processing based on the coping process. When the user can not cope with the abnormal state, e.g., a default of the apparatus, return processing in steps S12 to S11 continues so as to continuously display the error code.

In step S15, the control portion 2B determines whether or not reset operation is executed. When it is determined in step S15 that the reset operation is executed, the processing routine returns to step S2. When it is determined in step S15 that the reset operation is not executed, the processing routine returns to step S13. As mentioned above, when the abnormal state is found, the abnormal state is notified to the operator and processing for solving the abnormal state is implemented.

On the other hand, when it is determined in step S2 that the abnormal state is not found, in steps S3 to S5, the control portion 2B confirms whether or not associated equipment such as the foot switch 9 and the hand piece 8 is electrically connected.

In this case, when the control portion 2B confirms that the associated equipment is not electrically connected, in step S3, it is displayed to specify the non-connected equipment. In step S4, the user attaches the equipment. In step S5, the control portion 2B determines whether or not the foot switch 9 and the hand piece 8 are connected. When NO in step S5, the processing routine returns to step S3. When YES in step S5, the processing routine advances to step S6.

In other words, until the connection of the associated equipment is confirmed, the control portion 2B continues processing routine in steps S3 to S5.

Next, in steps S6 and S7, the control portion 2B checks whether or not the water supply tube 13 is connected. Specifically, in step S6, the control portion 2B sends to the operator, an instruction for attaching the water supply tube 13 to the water supply tube 5 by display operation or like. In step S7, the control portion 2B determines whether or not the water supply tube 13 is attached. In order to attach the water tube, the operator opens a door of the water supply pump 5, thereafter, the water supply tube 13 is attached, and the door is closed. That is, the non-opening and non-closing operation of the door of the water supply pump 5 before using means that the water supply tube 13 is not attached. Thus, the operation for paying attention is sent. Specifically, the door of the water supply pump 5 is set to the closing state from the opening state, then, the opening and closing detecting means is reset via the link mechanism (not shown), and a detecting signal (reset signal) is supplied to the control portion 2B. Therefore, when the reset signal is detected, the control portion 2B determines that the water supply tube 13 is attached. Then, the processing routine shifts to step S8. On the other hand, when the reset signal is not detected, the control portion 2B determines that the water supply tube 13 is not attached. Then, the processing routine returns to step S6.

Until the water supply tube 13 is attached, the control portion 2B displays such a fact that a tube needs to be attached by a character, sound and the like, further, the control portion 2B controls that the processing routine in steps S6 and S7 continues.

When the door is opened during the operation of the water supply pump 5, the detecting signal from the opening and closing detecting means is detected. Consequently, the control portion 2B controls the operation of the water supply pump 5 based on the detecting signal so that it interrupts. Incidentally, the opening and closing detecting means may have a function for detecting that the door is opened during the operation of the water supply pump 5 and for interrupting the operation of the water supply pump 5.

When the control portion 2B determines in step S7 that the water supply tube 13 is attached, in step S8, it controls the display operation so that the instruction for supplying the water is displayed on the operating and display panel 3. Thereafter, in step S9, it is determined whether or not a standby switch operation is performed by the operating and display panel 3 or foot switch 9. When it is determined in step S9 that it is performed, in step S10, the water supply pump 5 is driven so as to guide the water to the water supply tube 13.

When the water supply pump 5 is operated for an arbitrary time or more from the operating and display panel 3 or foot switch 9 of the water supply pump 5, the control portion 2B determines the completion of the operation for guiding the water to the water supply tube 13, and shifts to an available state.

Until the above-mentioned standby operation, the control portion 2B displays by the character or sound, such a message that the operation for guiding the water is necessary and further controls the operation so that the processing routine in steps S8 and S9 continues.

(Advantages)

According to the first embodiment, in the above-mentioned control example, the processing routine does not advance to the next step until the avoidance of a risk factor which is caused by an operating mistake upon using the apparatus. Thus, advantageously, the influence of the operating mistake is minimized. Further, it is possible to prevent the adverse influence to the organ in the coelom which is caused by the damage of the probe or the setting defect accompanied by the ultrasonic vibration. Therefore, the ultrasonic operating apparatus can always be used in a proper state and the ultrasonic operating apparatus can be provided with high safety.

Second Embodiment

Figure 4:
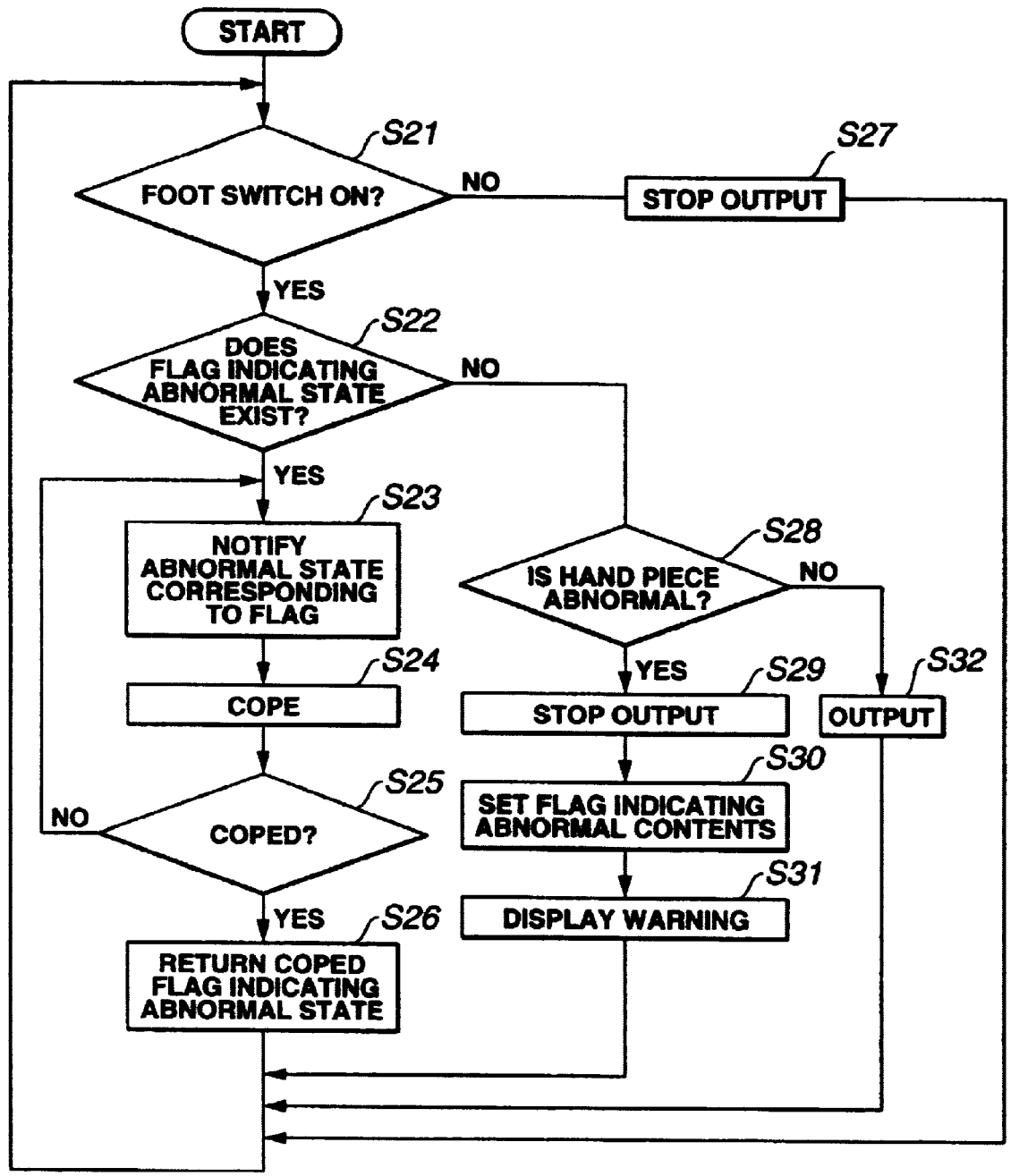
FIG. 4 is a flowchart showing an example of a control operation characterized by a control portion in the ultrasonic operating apparatus.

FIGS. 3 and 4 show an ultrasonic operating apparatus according to a second embodiment of the present invention. FIG. 3 is a block diagram showing the improved structure of a vibration driving circuit in an apparatus main body. FIG. 4 is a flowchart showing an example of a control operation characterized by a control portion in the ultrasonic operating apparatus. Referring to FIG. 3, the same components as those in the ultrasonic operating apparatus 1 according to the first embodiment are designated by the same reference numerals and are not described, and only different components are described.

(Structure)

According to the first embodiment, the description is given of the processing routine for the set-up operation to solve the user's operating mistake. However, it is effective in the case of detecting the abnormal state upon the initial check and use of the apparatus to use the above-mentioned process for solving the abnormal state in accordance with the proper processing routine by the user. In particular, the hand piece 8 is a portion which directly affects the patient. For example, in an abnormal state such as the break-off of the probe and short-circuit, importantly, the operation smoothly advances by indicating a process for user's exact recognition of the state and for solution of the abnormal state by coping.

Referring to FIG. 3, the vibration driving circuit 2A in the apparatus main body 2 has a constant-current loop including an output transfer 19 for disconnecting an output terminal and increasing a voltage, a detecting circuit 20 for detecting a voltage and current, a PLL circuit 21 for tracing a resonant frequency based on a voltage phase signal and a current phase signal from the detecting circuit 20, a D/A converter 22 for generating a signal for instructing the level of the ultrasonic output, a VCA circuit 23 for controlling the level of an AC signal from the PLL circuit 21 based on the signal from the D/A converter 22, a power amplifier 24 for amplifying an output from the VCA circuit 23 and generating power for driving the ultrasonic vibrator in the hand piece 8, and an operating amplifier 25 which compares the level of a current signal detected by the detecting circuit 20 with the level of the signal from the D/A converter 22.

Further, the vibration driving circuit 2A comprises a control portion 26 for controlling the operation of the apparatus main body 2 (corresponding to the control portion 2B), a relay 27 for turning on/off an output line of the vibration driving circuit 2A inserted between the connector 6 and the power amplifier 24, and an interface circuit 28 for transmitting an operating signal from the foot switch 9 to the control circuit 26 and the relay 27.

In the vibration driving circuit 2A with the above-mentioned structure, when the output terminal is set to ON by the foot switch 9, the information is transmitted to the control portion 26 via the interface circuit 28 and the control portion 26 sets the relay 27 to ON based on the transmitted information.

Then, under the PLL control operation, the output signal traced by the resonant frequency is transmitted to the output transfer 19 from the power amplifier 24 via the relay 27 and the detecting circuit 20, and the ultrasonic vibrator in the hand piece 8 is driven, thereby outputting an ultrasonic signal.

In this case, since the ultrasonic vibrator is driven by the constant current via the operating amplifier 25, the vibrating amplitudes are constantly maintained and stable processing is implemented.

Other structures are similar to those according to the first embodiment.

(Operation)

In the PLL circuit 21, the phase of the voltage signal matches the phase of the current signal near a resonant point to improve the output efficiency. Consequently, under the operation of the PLL circuit 21, the frequency changes and the resonant point is traced so that the difference in phases between the voltage signal and the current signal is null.

However, any abnormal state (here, break-off, crack, or crutch of the probe 10) loses a point without the difference in phase between the voltage and the current. Thus, the information on the abnormal state is transmitted to the control portion 26 from the PLL circuit 21, thereby detecting the abnormal state.

Alternatively, in the case of abnormally increasing the impedance (e.g., outputting the signal due to the contact state of the probe 10 with an foreign material such as a treatment tool or adding excessive power to the probe 10), when the voltage is increased to drive the ultrasonic vibrator and to ensure the current level, the resonant point is not traced. Namely, since the ultrasonic vibrator is not driven with the constant current, the information on the abnormal state is transmitted to the control portion 26.

When the abnormal state of the hand piece 8 is caused, the continuous use of the probe results in the damage due to the fatigue of the probe through the ultrasonic vibration. Consequently, the stable output might not be maintained. Preferably, a warning is sent to the user by an easily recognizable display process. Therefore, the proper coping process is displayed to the user and, advantageously, it is made different from the warning for another abnormal state to improve the recognizing property.

A detailed description is given of the processing routine for the above-mentioned coping process with reference to FIG. 4.

In the vibration driving circuit shown in FIG. 3, the control portion 26 first starts the processing routine shown in FIG. 4. Referring to FIG. 4, in step S21, the control portion 26 determines whether or not the foot switch 9 is ON. When YES in step S21, the processing routine advances to step S22. When NO in step S21, the relay 27 is opened through processing in step S27, thus, the control portion 26 controls the operation so that the output stops and, the processing routine returns to step S21.

When it is determined in step S21 that the foot switch 9 is ON, in step S22, the control portion 26 determines whether or not a trace for detecting the abnormal state is detected (whether or not a bit of a flag indicating an abnormal state is set). When YES in step S22, the processing routine advances to step S23. When NO in step S22, the processing routine shifts to step S28.

When NO in step S22, in step S28, the control portion 26 determines whether or not the abnormal state of the hand piece 8 is detected. When NO in step S28, in step S32, a predetermined signal is outputted and thereafter the processing routine returns to step S21. On the other hand, when YES in step S28, the output stops in step S29. In step S30, the bit of the flag indicating the abnormal state matching the abnormal contents is set. Then, in step S31, the control portion 26 displays the warning, reads the type of the abnormal state based on the flag indicating the abnormal state, and displays the read type on the operating and display panel 3. The type of abnormal state is specified by the bit of the flag indicating the abnormal state and the processing routine returns to step S21 while the corresponding warning contents are displayed.

When it is determined in step S22 that the trace for detecting the abnormal state is found, in step S23, the control portion 26 sends to the user a notification for the warning contents corresponding to the bit of the flag indicating the abnormal state by displaying them on the operating and display panel 3. In step S24, the coping process for solving the abnormal state is prompted to the user. In step S25, the control portion 26 determines whether or not the coping process is performed. When YES in step S25, the processing routine advances to step S26. When NO in step S25, the processing routine returns to step S23.

In other words, only in the case of completing the coping process, in step S26, the control portion 26 returns the bit corresponding to the flag indicating the abnormal state to 0. Then, the control portion 26 controls the operation so that the processing routine returns to step S21. Thus, when the abnormal state is solved, the probe 10 is normally used. Until the abnormal state is solved in steps S23 to S26, the control portion 26 controls the operation so that the operating and display panel 3 continuously displays the abnormal contents and the abnormal-state solving process.

(Advantages)

According to the second embodiment, as shown in the above-mentioned control example, the necessary loop is provided corresponding to each contents of the abnormal state. Further, when the abnormal state is generated in the coping step, the treatment is prohibited until the abnormal state is solved. Consequently, the abnormal state is certainly solved and a secondary default due to the abnormal state is prevented. Other advantages are the same as those according to the first embodiment.

The present invention is not limited to the first and second embodiments and can be applied to the combination and modifications of the first and second embodiments.

In this invention, it is apparent that various modifications different in a wide range can be made on this basis of this invention without departing from the spirit and scope of the invention. This invention is not restricted by any specific embodiment except being limited by the appended claims.

What is claimed is:

1. An ultrasonic operating apparatus comprising:
a hand piece having a vibration generating portion for generating ultrasonic vibrations;
an ultrasonic operating tool having a probe for transmitting the ultrasonic vibrations to the organ;
a signal generating portion which generates a driving signal for applying the ultrasonic vibrations to the vibration generating portion of the hand piece;
an electronic control portion which controls the driving signal and systematically controls the apparatus;
a detecting portion which detects an abnormal state of the ultrasonic operating tool; and
notifying means which notifies a user of detection of the abnormal state of the ultrasonic operating tool,
wherein the electronic control portion controls an operation so as to prevent additional control operations unless the abnormal state is corrected by a correct processing routine, the notifying means sends a notification indicating an incorrect processing routine to the user,
the electronic control portion determines whether or not a processing routine for correcting the abnormal state is available, if it is determined that the processing routine for correcting the abnormal state is available, the electronic control portion provides the user with the processing routine for correcting the abnormal state by way of the notifying means and if it is determined that the user cannot correct the detected abnormal state, the electronic control portion sends a notification indicating that the user cannot correct the detected abnormal state by the notifying means.

2. An ultrasonic operating apparatus according to claim 1, wherein the electronic control portion sends a notification by displaying a warning of the abnormal state of the ultrasonic operating tool upon detecting the abnormal state, different from a displaying operation of another abnormal state.

3. An ultrasonic operating apparatus according to claim 1, further comprising: water supply means which supplies water from a near portion of the probe in the ultrasonic operating tool, wherein the water supply means is operated only at a timing for operating a water supply function.

4. An ultrasonic operating apparatus according to claim 1, wherein an apparatus main body comprises the signal generating portion, the electronic control portion, the detecting portion, and the notifying means, the apparatus main body has a water supply pump for supplying water via a tube which connects the ultrasonic operating tool to a water supply passage in the hand piece and a guide mechanism for absorbing the difference depending a correcting process upon attaching the tube to the water supply pump.

5. An ultrasonic operating apparatus according to claim 1, wherein the electronic control portion performs initial check of an apparatus main body, and sends a notification indicating an abnormal state only upon detecting it by using the notifying means.

6. An ultrasonic operating apparatus according to claim 1, further comprising:
a foot switch for controlling the driving signal of the signal generating portion,
wherein the electronic control portion performs initial check of an apparatus main body, when the abnormal state is not found, determines whether or not the foot switch and the hand piece are connected to the apparatus main body and, when it is determined that they are not connected, sends a notification indicating which of the foot switch and the hand piece is not connected to the apparatus main body to the user by using the notifying means.

7. An ultrasonic operating apparatus according to claim 1, further comprising:
a foot switch for controlling the driving signal of the signal generating portion,
wherein the electronic control portion determines whether the foot switch is ON or OFF and, when it determines that it is OFF, the electronic control portion stops the generation of the driving signal from the signal generating portion.

8. An ultrasonic operating apparatus according to claim 7, wherein the electronic control portion monitors whether or not the ultrasonic operating tool is abnormal when the foot switch is ON and, when it is monitored that it is abnormal, the electronic control portion sends a notification indicating the abnormal state until a user corrects the abnormal state.

9. An ultrasonic operating apparatus according to claim 7, wherein the electronic control portion monitors whether or not the ultrasonic operating tool is abnormal when the foot switch is ON and, when it is monitored that it is abnormal, the electronic control portion stops the generation of the driving signal from the signal generating portion and sends a notification indicating the abnormal state by the notifying means.

10. An ultrasonic operating apparatus according to claims 8 or 9, wherein when the abnormal state of the ultrasonic operating tool is solved, the electronic control portion enables the signal generating portion to output the driving signal.

11. An ultrasonic operating apparatus according to any one of claims 1-5 or 6-9, wherein the detecting portion includes a PLL circuit for making a resonant frequency of the driving signal supplied to the ultrasonic operating tool constant and, when the PLL circuit changes the resonant frequency, the detecting portion detects the abnormal state of the ultrasonic operating tool.

12. An ultrasonic operating apparatus according to any one of claims 1-5 or 6-9, wherein the notifying means includes the display panel for visual notification and a sound production portion for auditory notification, in order to specify the abnormal state of the ultrasonic operating tool.

13. An ultrasonic operating apparatus having an ultrasonic operating tool, comprising:
a detecting means for detecting an abnormal state of the ultrasonic operating tool;
notifying means for notifying a user of detection of the abnormal state of the ultrasonic operating tool; and
an electronic control portion which controls a driving signal and controls the apparatus, the electronic control portion suspending operation of the ultrasonic operation tool when the abnormal state is detected until the abnormal state is corrected,
the electronic control portion, upon detection of the abnormal state, determines whether or not a processing routine for correcting the abnormal state is available, if it is determined that the processing routine for correcting the abnormal state is available, the electronic control portion provides the user with the processing routine for correcting the abnormal state by way of the notifying means and if it is determined that the user cannot correct the detected abnormal state, the electronic control portion sends a notification indicating that the user cannot correct the detected abnormal state by the notifying means, and
the electronic control portion prevents execution of control of the ultrasonic operation tool unless the user corrects the abnormal state by the correct procedure.

14. A method for controlling an ultrasonic operating tool, comprising:
detecting an abnormal state of an ultrasonic operating tool;
notifying a user of detection of the abnormal state of the ultrasonic operating tool;
suspending operation of the ultrasonic operation tool when the abnormal operating state is detected;
determining whether or not a processing routine for correcting the abnormal state is available;
providing the user with the processing routine for correcting the abnormal state if it is determined that the processing routine for correcting the abnormal state is available by way of notifying means and if it is determined that the user cannot correct the detected abnormal state, the electronic control portion sends a notification indicating that the user cannot correct the detected abnormal state by the notifying means; and
preventing operation of the ultrasonic operation tool unless the user corrects the abnormal operating state by the correct processing routine.

* * * * *